US011149222B2

(12) United States Patent
Wright et al.

(10) Patent No.: US 11,149,222 B2
(45) Date of Patent: Oct. 19, 2021

(54) XANTHENES AS FUEL MARKERS

(71) Applicants: Dow Global Technologies LLC, Midland, MI (US); Rohm and Haas Company, Collegeville, PA (US)

(72) Inventors: Robert J. Wright, Sugar Land, TX (US); Brian A. Jazdzewski, Houston, TX (US); Warren E. Smith, Buckinghamshire (GB); Jeremy Chris Reyes, Lake Jackson, TX (US); Zahid Asif, Royersford, PA (US); Clark H. Cummins, Midland, MI (US); William L. Winniford, Lake Jackson, TX (US)

(73) Assignees: DOW GLOBAL TECHNOLOGIES LLC, Midland, MI (US); ROHM AND HAAS COMPANY, Collegeville, PA (US)

( * ) Notice: Subject to any disclaimer, the term of this patent is extended or adjusted under 35 U.S.C. 154(b) by 0 days.

(21) Appl. No.: 16/975,233

(22) PCT Filed: Mar. 25, 2019

(86) PCT No.: PCT/US2019/023849
§ 371 (c)(1),
(2) Date: Aug. 24, 2020

(87) PCT Pub. No.: WO2019/195013
PCT Pub. Date: Oct. 10, 2019

(65) Prior Publication Data
US 2021/0009909 A1    Jan. 14, 2021

Related U.S. Application Data

(60) Provisional application No. 62/652,946, filed on Apr. 5, 2018.

(51) Int. Cl.
*C10L 1/00*      (2006.01)
*C07D 311/82*   (2006.01)
*C10L 1/185*    (2006.01)

(52) U.S. Cl.
CPC ............ *C10L 1/003* (2013.01); *C07D 311/82* (2013.01); *C10L 1/1855* (2013.01); *C10L 2200/0446* (2013.01); *C10L 2200/0453* (2013.01); *C10L 2200/0469* (2013.01); *C10L 2230/16* (2013.01)

(58) Field of Classification Search
CPC .................. C10L 1/003; C10L 1/1855; C10L 2200/0446; C10L 2200/0453; C10L 2200/0469; C10L 2230/16; C07D 311/82
See application file for complete search history.

(56) References Cited

U.S. PATENT DOCUMENTS

| 3,522,275 A * | 7/1970 | Finkbeiner | C07F 7/1804 549/388 |
| 3,931,232 A * | 1/1976 | Bender | C07D 311/82 549/388 |
| 5,101,059 A * | 3/1992 | Carpino | C07C 43/168 549/388 |
| 5,145,573 A * | 9/1992 | Riedel | C10M 171/007 208/14 |
| 5,434,272 A * | 7/1995 | Corrie | C07D 207/452 548/525 |
| 5,498,808 A * | 3/1996 | Smith | C10L 1/14 585/3 |
| 5,554,770 A * | 9/1996 | Caruso | C07D 311/82 549/388 |
| 5,672,182 A * | 9/1997 | Smith | C10L 1/003 44/349 |
| 6,162,931 A * | 12/2000 | Gee | C07C 37/055 430/345 |
| 6,811,575 B2 | 11/2004 | Ho et al. | |
| 6,991,914 B2 * | 1/2006 | Park | C07D 265/38 435/19 |
| 8,961,624 B2 | 2/2015 | Green et al. | |
| 9,005,314 B2 | 4/2015 | Green et al. | |
| 9,079,838 B2 | 7/2015 | Green et al. | |
| 9,222,928 B2 | 12/2015 | Green et al. | |

(Continued)

FOREIGN PATENT DOCUMENTS

EP    1479749           11/2004
JP    60088087 A *      5/1985

(Continued)

OTHER PUBLICATIONS

Aizenshtat et al., Israel Journal of Chemistry, 1972, pp. 753-763.
Guodong Shen et al., RSC Adv., 2016, pp. 84748-84751, vol. 6.
Hermann Franke et al., Journal Fuer Praktische Chemie, 1967, pp. 249-261.
Karl Ziegler et al., Berichte Der Deutschen Chemischen Gesellschaft (Abteilung) B: Abhandlungen, 1922, pp. 2257-2277.
Maneewattanapinyo, Chulalongkorn University, Faculty of Science, 2002, pp. FP-122.
Masanori Wada et al., Bulletin of the Chemical Society of Japan, 1999, pp. 779-785.
Morisaki, Y et al., Journal of Polymer Science Part A: Polymer Chemistry, 2014, pp. 2815-2821, vol. 52.
PCT/US2019/023849, International Search Report and Written Opinion dated Jul. 9, 2019.

*Primary Examiner* — Pamela H Weiss

(57) ABSTRACT

A method for marking a petroleum hydrocarbon or a liquid biologically derived fuel; said method comprising adding to said petroleum hydrocarbon or liquid biologically derived fuel at least one compound that is a $R^1$, $R^2$, $R^3$, $R^4$, $R^5$, $R^6$, $R^7$, $R^8$, $R^9$ and $R^{10}$-substituted xanthene, wherein $R^1$, $R^2$, $R^3$, $R^4$, $R^5$, $R^6$, $R^7$, $R^8$, $R^9$ and $R^{10}$ independently are hydrogen, hydrocarbyl, hydrocarbyloxy, aryl or aryloxy; wherein each compound of formula (I) is present at a level from 0.01 ppm to 20 ppm.

7 Claims, No Drawings

(56) References Cited

U.S. PATENT DOCUMENTS

| | | |
|---|---|---|
| 9,371,497 B2 | 6/2016 | Swedo |
| 9,422,493 B2 | 8/2016 | Butterick, III et al. |
| 9,587,187 B2 | 3/2017 | Butterick, III et al. |
| 9,688,930 B2 | 6/2017 | Green et al. |
| 9,926,506 B2 | 3/2018 | Green et al. |
| 10,131,606 B2 | 11/2018 | Green et al. |
| 2003/0126694 A1 | 7/2003 | Ho et al. |
| 2004/0110302 A1 | 6/2004 | Vamvakaris et al. |
| 2004/0250469 A1 | 12/2004 | Baxter et al. |

FOREIGN PATENT DOCUMENTS

| | | | | |
|---|---|---|---|---|
| WO | WO-0204431 A1 * | 1/2002 | ............ | C10L 1/2335 |
| WO | 2002068434 | 9/2002 | | |
| WO | WO-2005063730 A1 * | 7/2005 | ........... | C07D 311/82 |

\* cited by examiner

XANTHENES AS FUEL MARKERS

This invention relates to a new method for marking liquid hydrocarbons and other fuels and oils, as well as new compounds useful for this purpose.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 9,587,187 discloses the use of trityl aryl ethers for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a method for marking a petroleum hydrocarbon or a liquid biologically derived fuel; said method comprising adding to said petroleum hydrocarbon or liquid biologically derived fuel at least one compound of formula (I)

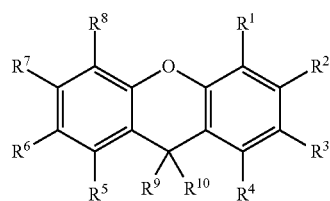

(I)

wherein $R^1$, $R^2$, $R^3$, $R^4$, $R^5$, $R^6$, $R^7$, $R^8$, $R^9$ and $R^{10}$ independently are hydrogen, hydrocarbyl, hydrocarbyloxy, aryl or aryloxy; wherein each compound having formula (I) is present at a level from 0.01 ppm to 20 ppm.

The present invention further provides a compound of formula (II)

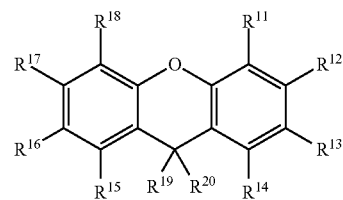

wherein $R^{11}$, $R^{12}$, $R^{13}$, $R^{14}$, $R^{15}$, $R^{16}$, $R^{17}$, $R^{18}$ independently are hydrogen, hydrocarbyl, hydrocarbyloxy, aryl or aryloxy; $R^{19}$ and $R^{20}$ independently are hydrocarbyl, hydrocarbyloxy, aryl or aryloxy; provided that at least one of $R^{11}$, $R^{12}$, $R^{13}$, $R^{14}$, $R^{15}$, $R^{16}$, $R^{17}$, $R^{18}$, $R^{19}$ and $R^{20}$ contains at least seven carbon atoms; and that $R^{11}$, $R^{12}$, $R^{13}$, $R^{14}$, $R^{15}$, $R^{16}$, $R^{17}$, $R^{18}$, $R^{19}$ and $R^{20}$ collectively contain fewer than 20 carbon atoms.

DETAILED DESCRIPTION

Percentages are weight percentages (wt %) and temperatures are in ° C., unless specified otherwise. Experimental work is carried out at room temperature (20-25° C.), unless otherwise specified. Concentrations expressed in parts per million ("ppm") are calculated on a weight/volume basis (mg/L). The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." A "hydrocarbyl" group is a substituent derived from an aliphatic hydrocarbon, which may be linear, branched or cyclic and which may have one or more hydroxyl or alkoxy substituents. Preferably, hydrocarbyl groups are unsubstituted. An "alkyl" group is a substituted or unsubstituted saturated hydrocarbyl group having a linear, branched or cyclic structure. Alkyl groups may have one or more aryl, hydroxyl or alkoxy substituents. Preferably, alkyl groups are unsubstituted. Preferably, alkyl groups are linear or branched, i.e., acyclic. Preferably, each alkyl substituent is not a mixture of different alkyl groups, i.e., it comprises at least 98% of one particular alkyl group. An "alkenyl" group is a substituted or unsubstituted hydrocarbyl group having a linear, branched or cyclic arrangement and having at least one carbon-carbon double bond. Preferably, alkenyl groups have no more than three carbon-carbon double bonds, preferably no more than two, preferably one. Alkenyl groups may have one or more hydroxyl or alkoxy substituents. Preferably, alkenyl groups are unsubstituted. Preferably, alkyl and alkenyl groups are linear or branched, i.e., acyclic. An "aryl" group is a substituent derived from an aromatic hydrocarbon which may have aliphatic carbon atoms as well as aromatic carbon atoms. An aryl group may be attached via an aromatic ring carbon atom or via an aliphatic carbon atom. Aryl groups may have one or more hydroxyl or alkoxy substituents. A "hydrocarbyloxy," "alkoxy," "alkenyloxy" or "aryloxy" group is a substituent formed by adding an oxygen atom at the point of attachment of a hydrocarbyl, alkyl, alkenyl or aryl group, respectively (e.g., between an alkyl group and a dibenzofuran carbon atom). The number of carbon atoms in a substituent includes any carbon atoms which may be in alkyl or alkoxy substituents thereof. Preferably, the compounds of this invention contain elements in their naturally occurring isotopic proportions.

Preferably, $R^1$, $R^2$, $R^3$, $R^4$, $R^5$, $R^6$, $R^7$, $R^8$, $R^9$ and $R^{10}$ collectively contain at least one carbon atom, preferably at least two, preferably at least three, preferably at least four. Preferably, $R^1$, $R^2$, $R^3$, $R^4$, $R^5$, $R^6$, $R^7$, $R^8$, $R^9$ and $R^{10}$ collectively have no more than 60 carbon atoms, preferably no more than 50, preferably no more than 40, preferably no more than 35. Preferably, at least one of $R^1$, $R^2$, $R^3$, $R^4$, $R^5$, $R^6$, $R^7$, $R^8$, $R^9$ and $R^{10}$ has at least two carbon atoms, preferably at least three, preferably at least four, preferably at least five, preferably at least six. Preferably, hydrocarbyl groups are alkyl or alkenyl groups, preferably alkyl groups. Preferably, hydrocarbyloxy groups are alkoxy or alkenyloxy groups, preferably alkoxy groups.

Preferably, $R^1$, $R^2$, $R^3$, $R^4$, $R^5$, $R^6$, $R^7$, $R^8$, $R^9$ and $R^{10}$ independently are hydrogen, $C_1$-$C_{30}$ hydrocarbyl, $C_1$-$C_{30}$ hydrocarbyloxy, $C_6$-$C_{35}$ aryl or $C_6$-$C_{35}$ aryloxy; preferably hydrogen, $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{30}$ aryl or $C_6$-$C_{30}$ aryloxy; preferably hydrogen, $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{20}$ aryl or $C_6$-$C_{20}$ aryloxy; preferably hydrogen, $C_1$-$C_{30}$ alkyl or $C_2$-$C_{30}$ alkenyl; preferably hydrogen, $C_1$-$C_{25}$ alkyl or $C_2$-$C_{25}$ alkenyl; preferably hydrogen or $C_1$-$C_{25}$ alkyl; preferably hydrogen or $C_1$-$C_{22}$ alkyl. Preferably, alkyl groups having at least 3 carbon atoms are linear or branched, i.e., not cyclic. In a preferred embodiment of the invention, at least one of $R^1$, $R^8$, $R^9$ and $R^{10}$ is alkyl, and $R^2$, $R^3$, $R^4$, $R^5$, $R^6$ and $R^7$ are hydrogen.

In using the compounds described herein as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm, preferably 0.5 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline. Preferably, the marker compound is added as a solution in a solvent, preferably a hydrocarbon solvent.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

In the compound of formula (II), $R^{11}$, $R^{12}$, $R^{13}$, $R^{14}$, $R^{15}$, $R^{16}$, $R^{17}$, $R^{18}$ independently are hydrogen, $C_1$-$C_{30}$ hydrocarbyl, $C_1$-$C_{30}$ hydrocarbyloxy, $C_6$-$C_{35}$ aryl or $C_6$-$C_{35}$ aryloxy; preferably hydrogen, $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{30}$ aryl or $C_6$-$C_{30}$ aryloxy; preferably hydrogen, $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{20}$ aryl or $C_6$-$C_{20}$ aryloxy; preferably hydrogen, $C_1$-$C_{30}$ alkyl or $C_2$-$C_{30}$ alkenyl; preferably hydrogen, $C_1$-$C_{25}$ alkyl or $C_2$-$C_{25}$ alkenyl; preferably hydrogen or $C_1$-$C_{25}$ alkyl; preferably hydrogen or $C_1$-$C_{22}$ alkyl. Preferably, $R^{19}$ and $R^{20}$ independently are $C_1$-$C_{30}$ hydrocarbyl, $C_1$-$C_{30}$ hydrocarbyloxy, $C_6$-$C_{35}$ aryl or $C_6$-$C_{35}$ aryloxy; preferably $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{30}$ aryl or $C_6$-$C_{30}$ aryloxy; preferably $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{20}$ aryl or $C_6$-$C_{20}$ aryloxy; preferably $C_1$-$C_{30}$ alkyl or $C_2$-$C_{30}$ alkenyl; preferably $C_1$-$C_{25}$ alkyl or $C_2$-$C_{25}$ alkenyl; preferably $C_1$-$C_{25}$ alkyl; preferably $C_1$-$C_{22}$ alkyl. Preferably, alkyl groups having at least 3 carbon atoms are linear or branched, i.e., not cyclic. Preferably, $R^{12}$, $R^{13}$, $R^{14}$, $R^{15}$, $R^{16}$, and $R^{17}$ independently are hydrogen or $C_1$-$C_4$ alkyl, preferably hydrogen. In a preferred embodiment of the invention, at least two of $R^{11}$, $R^{18}$, $R^{19}$ and $R^{20}$ are alkyl, preferably at least three, and $R^{12}$, $R^{13}$, $R^{14}$, $R^{15}$, $R^{16}$, and $R^{17}$ are hydrogen. Preferably, at least one of $R^{11}$, $R^{12}$, $R^{13}$, $R^{14}$, $R^{15}$, $R^{16}$, $R^{17}$, $R^{18}$, $R^{19}$ and $R^{20}$ has at least eight carbon atoms, preferably at least nine carbon atoms. Preferably, $R^{11}$, $R^{12}$, $R^{13}$, $R^{14}$, $R^{15}$, $R^{16}$, $R^{17}$, $R^{18}$, $R^{19}$ and $R^{20}$ collectively contain fewer than 19 carbon atoms, preferably fewer than 18, preferably fewer than 17, preferably fewer than 16. In a preferred embodiment of the invention both $R^{19}$ and $R^{20}$ are $C_1$-$C_{22}$ alkyl; preferably both are $C_7$-$C_{22}$ alkyl, preferably $C_8$-$C_{22}$ alkyl. In a preferred embodiment of the invention, $R^{19}$ and $R^{20}$ are $C_1$-$C_4$ alkyl and at least one of $R^{11}$ or $R^{18}$ is $C_7$-$C_{16}$ alkyl, preferably $C_8$-$C_{16}$ alkyl.

The compounds of this invention may be prepared by methods known in the art, e.g., allowing xanthene or a substituted xanthene (e.g., 9,10-dimethylxanthene) to react with a strong base (e.g., alkyllithiums) to form a deprotonated precursor, then allowing said precursor to react with a compound having a carbon-halogen bond.

EXAMPLES

Synthesis of Markers

Synthesis of 9-ethyl-9H-xanthene (3) and 9-hexyl-9H-xanthene (4)

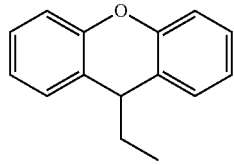

3

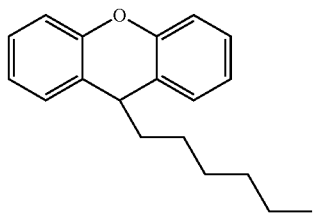

4

A 150 mL Schlenk flask was charged with xanthene (2 g, 11 mmol) and THF (75 mL). The stirred solution was cooled in an ice-bath and n-buLi (1.6 M in hexane, 7.5 mL) was slowly added over 2 minutes. The mixture was stirred at 0° C. for 30 min and ethyl iodide (2.05 g, 13.17 mmol) was added. The reaction was allowed to stir for 1 h. The reaction was quenched with $H_2O$ (150 mL). The contents were placed in a separatory funnel and extracted with $Et_2O$ (250 mL). The organic phase was isolated, dried ($Na_2SO_4$), filtered, and concentrated under reduced pressure. Purification was performed by column chromatography using hexane as the eluent. Mass of isolated product was 1.15 grams (49.8%). $^1$H NMR (400 MHz, Chloroform-d) δ 7.22-7.13 (m, 4H), 7.08 6.98 (m, 4H), 3.92 (t, J=5.7 Hz, 1H), 1.75 (qd, J=7.4, 5.7 Hz, 2H), 0.72 (t, J=7.4 Hz, 3H). $^{13}$C NMR (101 MHz, Chloroform-d) δ 152.47, 128.77, 128.73, 127.55, 125.28, 123.14, 116.40, 116.34, 40.11, 33.60, 9.86.

Synthesis of 9-hexyl-9H-xanthene (4) was performed the same way but with hexyl bromide. Yield=1.60 grams (54.8%). $^1$H NMR (400 MHz, Chloroform-d) δ 7.23-7.11 (m, 4H), 7.09-6.97 (m, 4H), 3.92 (t, J=6.1 Hz, 1H), 1.67 (dt, J=8.3, 6.0 Hz, 2H), 1.38-1.04 (m, 8H), 0.79 (t, J=6.8 Hz, 3H). $^{13}$C NMR (101 MHz, Chloroform-d) δ 152.40, 128.72, 127.49, 125.89, 123.14, 116.42, 40.96, 39.22, 31.85, 29.42, 25.60, 22.77, 14.19.

Synthesis of 9,9-dihexyl-9H-xanthene (5)

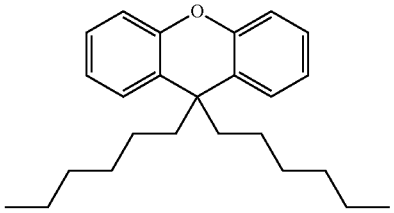

5

Compound 5 was synthesized as reported in the Journal of Polymer Science, Part A: Polymer Chemistry, 52(19), 2815-2821; 2014

Synthesis of 4-dodecyl-9,9-dimethyl-9H-xanthene (6)

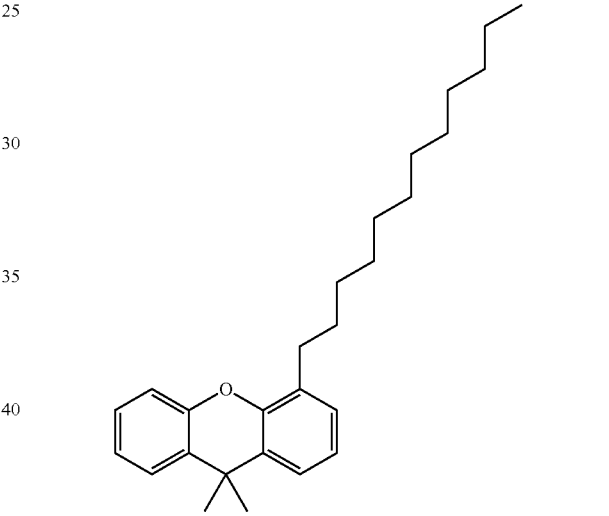

6

A 150 mL Schlenk flask was charged with 9,9-dimethylxanthene (3 g, 14.26 mmol), a stir bar, and THF (75 mL; anhydrous and degassed). The flask was cooled to −78° C. on a dry ice-acetone bath. To the flask, n-BuLi (9.8 mL of n-BuLi in hexane; 1.6 M) was added via syringe over 2 min. The flask was carefully removed from the dry ice-acetone bath and allowed to stir for 30 mins. The flask was then resubmerged in the dry ice-acetone bath. To the flask, dodecyl iodide (4.42 g, 14.26 mmol) was added over 1 min via syringe. The reaction was allowed to stir and warm to room temperature overnight. The reaction was quenched with water (150 mL) and the mixture was extracted with $CH_2Cl_2$ (250 mL). The organic fraction was dried ($Na_2SO_4$), filtered, and the solvent was removed on a rotary evaporator. The product was purified by column chromatography on a 340 g silica Biotage column using a gradient of 0-5% $CH_2Cl_2$ in hexane as the eluent. Mass of product as a colorless liquid=0.8 g (14.8%)

Laundering 5 and Analysis

A sample of 5 was made at 3 mg/l concentration in diesel that was treated with basic alumina and filtered. The marked diesel sample was mixed with laundering agent in the desired ratio. A magnetic stir bar was added to the sample and arranged on a multi position magnetic stir plate. All samples were stirred for 4 hours at 200 rpm. After four hours all samples was let to settle for 30 minutes. An aliquot was taken from top and filtered through a 0.45 micron PTFE, filter. Laundered samples along with controls not exposed to laundering were analyzed by GC/MS with the parameters below Agilent 6890 Gas Chromatograph
Autosampler: Agilent 7683B Series
Detector: Agilent MSD 5973N mass spectroscopy detector
Column: DB-35MS, 15-m×0.25-mm ID, 0.25-μm film
Oven: Initial temperature 100° C.
Ramp 1 at 10° C./minute to 280° C., hold 0 min
Ramp 2 at 10° C./minute to 320° C., hold 5 min
Injection port: 280° C.
Transfer line: 280° C.
Injection Mode: Splitless
Carrier gas: Helium
Column flow rate: 1.4 mL/min, constant flow mode
Purge time: 20 min
Purge flow: 20 mL/min
Viscosity delay: 1
Injection volume: 1 μL
Acquisition mode: SIM
Solvent delay: 13 min
MS quad: 200° C.
MS source: 250° C.

| Laundering Agent | Comments | 5 |
|---|---|---|
| Al Oxide-Neutral | 5% w/v | 93.5 |
| Al Oxide-Basic | 5% w/v | 103.4 |
| Bentonite | 5% w/v | 107.8 |
| HCl Conc. | 5% w/v | 101.2 |
| Fuller's Earth | 5% w/v | 99.5 |
| $H_2O_2$ –30% | 50 v/v | 96.1 |
| Silica Gel | 5% w/v | 100.6 |
| NaOCl (5%-bleach) | 5% w/v | 101.6 |
| Activated carbon | 5% w/v | 95.8 |
| Methanol | 50% v/v | 106.3 |
| Acetonitrile | 50% v/v | 103.9 |
| $H_2SO_4$ Conc. | 5% w/V | 107.1 |
| $HNO_3$ Conc. | 5% w/v | 106.8 |

Laundering and Analysis of Xanthene (1), 9,9-dimethyl-9H-xanthene (2), 3, 4, and 6

Samples were made at 10 mg/l concentration in diesel that was treated with basic alumina and filtered. The marked diesel samples were mixed with laundering agent in the specified ratio. A magnetic stir bar was added to the sample and arranged on a multi position magnetic stir plate. All samples were stirred for 4 hours at 200 rpm. After four hours all samples were let to settle for 30 minutes. An aliquot was taken from top and filtered through syringe with 0.45 micron PTFE filter. Laundered samples along with control which was not exposed to laundering were analyzed by GC/MS as described below Quantitative analysis and separation of fuel markers from fuel matrix was achieved with two-dimensional heartcutting gas chromatography method. A Deans Switch based on capillary flow technology is used to afford in-oven heartcutting capability. The method employs a DB-17HT column (15 m×250 μm×0.15 μm) in the first dimension (D1) and a VF-WAXms column (30 m×250 μm×1.0 μm) in the second dimension (D2). A flame ionization detector (FID) was used as the detector in D1 and a mass selective detector (MSD) was used for low level detection of markers the D2 column using single-ion monitoring (SIM) mode. The retention times of the markers in D1 which determine the heartcutting time was obtained using standards in xylenes. The full mass spectra of the individual markers were obtained to determine the most selective ion fragment that gave the best sensitivity and selectivity for analysis of markers in fuel matrix. Quantitation was performed using multi-point external calibration.

| Laundering Agent | Comments | 1 | 2 | 3 | 4 | 6 |
|---|---|---|---|---|---|---|
| Adsorbents | | | | | | |
| Al Oxide-Neutral | 5% w/v | 95% | 100% | 100% | 97% | 97% |
| Al Oxide-Basic | 5% w/v | 99% | 99% | 102% | 98% | 101% |
| Bentonite | 5% w/v | 96% | 102% | 105% | 99% | 92% |
| Silica Gel | 5% w/v | 89% | 94% | 100% | 97% | 95% |
| Fuller's Earth | 5% w/v | 99% | 100% | 100% | 100% | 87% |
| Activated carbon | 5% w/v | 90% | 96% | 48% | 95% | 100% |
| Bases | | | | | | |
| KOH (40%) | 5% w/v | 104% | 103% | 107% | 110% | 93% |
| NaOH (40%) | 5% w/v | 104% | 103% | 105% | 105% | 100% |
| NaOMe (30% weight) in MeOH | 5% w/v | 102% | 102% | 78% | 98% | 91% |
| KOH and MPEG 350 (0.5% weight) | 5% w/v | 92% | 100% | 50% | 90% | 91% |
| Acids | | | | | | |
| $H_2SO_4$ Conc. | 5% w/v | 59% | 94% | 12% | 100% | 95% |
| $HNO_3$ Conc. | 5% w/v | 2% | 95% | 2% | 2% | 94% |
| HCl Conc. | 5% w/v | 102% | 102% | 109% | 103% | 101% |
| Oxidants | | | | | | |
| $H_2O_2$ 30% | 5% v/v | 95% | 101% | 106% | 102% | 106% |
| Bleach (commercial) | 5% v/v | 90% | 101% | 61% | 92% | 107% |
| Solvents | | | | | | |
| Methanol | 50% v/v | 106% | 102% | 108% | 103% | 103% |
| Acetonitrile | 50% v/v | 97% | 76% | 97% | 100% | 106% |
| Temperature | | | | | | |
| –30 C. | 4 h and filter | 96% | 100% | 107% | 101% | 108% |
| 60 C. | 4 h and filter | 100% | 101% | 104% | 100% | 100% |

The invention claimed is:

1. A method for marking a petroleum hydrocarbon or a liquid biologically derived fuel; said method comprising adding to said petroleum hydrocarbon or liquid biologically derived fuel at least one compound of formula (I)

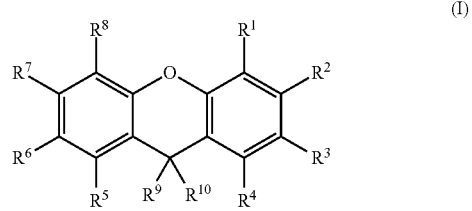

wherein $R^1$, $R^2$, $R^3$, $R^4$, $R^5$, $R^6$, $R^7$, $R^8$, $R^9$ and $R^{10}$ independently are hydrogen, hydrocarbyl, hydrocarbyloxy, aryl or aryloxy; wherein each compound of formula (I) is present at a level from 0.01 ppm to 20 ppm.

2. The method of claim 1 in which $R^1$, $R^2$, $R^3$, $R^4$, $R^5$, $R^6$, $R^7$, $R^8$, $R^9$ and $R^{10}$ independently are hydrogen, $C_1$-$C_{30}$ hydrocarbyl, $C_1$-$C_{30}$ hydrocarbyloxy, $C_6$-$C_{35}$ aryl or $C_6$-$C_{35}$ aryloxy.

3. The method of claim 2 in which $R^1$, $R^2$, $R^3$, $R^4$, $R^5$, $R^6$, $R^7$, $R^8$, $R^9$ and $R^{10}$ collectively have at least one carbon atom.

4. The method of claim 3 in which $R^1$, $R^2$, $R^3$, $R^4$, $R^5$, $R^6$, $R^7$, $R^8$, $R^9$ and $R^{10}$ independently are hydrogen, $C_1$-$C_{30}$ alkyl, $C_2$-$C_{30}$ alkenyl, $C_1$-$C_{30}$ alkoxy, $C_2$-$C_{30}$ alkenyloxy, $C_6$-$C_{20}$ aryl or $C_6$-$C_{20}$ aryloxy.

5. The method of claim 4 in which the compound of formula (I) is present at a level from 0.01 ppm to 10 ppm.

6. The method of claim 5 in which $R^1$, $R^2$, $R^3$, $R^4$, $R^5$, $R^6$, $R^7$, $R^8$, $R^9$ and $R^{10}$ independently are hydrogen or $C_1$-$C_{25}$ alkyl.

7. The method of claim 6 in which at least one of $R^1$, $R^8$, $R^9$ and $R^{10}$ is alkyl, and $R^2$, $R^3$, $R^4$, $R^5$, $R^6$ and $R^7$ are hydrogen.

* * * * *